US006307046B1

(12) United States Patent
Tanaka et al.

(10) Patent No.: US 6,307,046 B1
(45) Date of Patent: Oct. 23, 2001

(54) METHOD FOR MODIFYING MELAMINE DERIVATIVES

(75) Inventors: Norio Tanaka; Hiroyuki Kousaka; Yasuyuki Nakajima, all of Funabashi; Kouichi Masahashi; Takashi Kitabayashi, both of Nei-gun, all of (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 09/600,122

(22) PCT Filed: Jan. 18, 1999

(86) PCT No.: PCT/JP99/00123

§ 371 Date: Jul. 31, 2000

§ 102(e) Date: Jul. 31, 2000

(87) PCT Pub. No.: WO99/36411

PCT Pub. Date: Jul. 22, 1999

(30) Foreign Application Priority Data

Jan. 19, 1998 (JP) .................................. 10-007220
Jan. 20, 1998 (JP) .................................. 10-008263

(51) Int. Cl.$^7$ .................................................. C07D 251/70
(52) U.S. Cl. .......................................... 544/196; 544/204
(58) Field of Search .................................... 544/196, 204

(56) References Cited

U.S. PATENT DOCUMENTS

| 4,618,676 | 10/1986 | Ebel et al. | ............................... 544/196 |
| 4,668,785 | 5/1987 | Ebel et al. | ............................... 544/196 |
| 4,886,882 | 12/1989 | Ebel et al. | ............................... 544/196 |
| 5,792,867 | * 8/1998 | Tanaka et al. | ........................ 544/196 |
| 6,127,538 | * 10/2000 | Tanka et al. | .......................... 544/196 |

FOREIGN PATENT DOCUMENTS

| 0 711 760 A1 | 5/1996 | (EP) . |
| 0 760 369 A1 | 3/1997 | (EP) . |
| 0 882 720 A1 | 12/1998 | (EP) . |
| 3-215564 | 9/1991 | (JP) . |
| 8-27125 | 1/1996 | (JP) . |
| 8-27128 | 1/1996 | (JP) . |
| 8-193071 | 7/1996 | (JP) . |
| 8-272125 | 10/1996 | (JP) . |
| 10-231291 | 9/1998 | (JP) . |

OTHER PUBLICATIONS

Hudlicky, Milos., Reductions in Organic Chemistry, 4–8, 10–12, 40, 49, 62–63, 666–69, 1984.*

Pacquette L. A., Encyclopedia of Reagents fro Organic Synthesis 1257–1258, 3785, 4401–4402, 1995.*

Fieser and Fieser, Reagents for Organic Synthesis vol. 1, p. 140, 1965.*

* cited by examiner

*Primary Examiner*—Mukund J. Shah
*Assistant Examiner*—Venkataraman Balasubramanian
(74) *Attorney, Agent, or Firm*—Oliff & Berridge, PLC

(57) ABSTRACT

The present invention provides a method for modifying melamine derivatives that can produce N-substituted melamine derivatives by introducing a substituent group to melamine or N-substituted melamine derivatives. The method is characterized by heating melamine or an N-substituted melamine derivative and an alcohol in the presence of a mixed catalyst comprising a hydrogenation catalyst and a dehydrogenation catalyst and hydrogen to allow reaction or heating melamine or an N-substituted melamine derivative and an alcohol in the presence of a hydrogenation catalyst and hydrogen with addition/coexistence of a metal to allow reaction. The compound groups obtained by introducing a substituent group to the amino group of melamine derivative with an alcohol by the method of the present invention can be used widely as intermediates of fine chemicals such as various agricultural chemicals, medicines, dyes, paints, etc. and as various resin materials and flame retardant materials.

13 Claims, No Drawings

METHOD FOR MODIFYING MELAMINE DERIVATIVES

TECHNICAL FIELD

The present invention relates to an improvement of a method for modifying melamine derivatives by introducing substituents on the N atom of melamine or an N-substituted melamine derivative, characterized by heating melamine or an N-substituted melamine derivative and an alcohol in the presence of a metal catalyst and hydrogen to allow reaction.

A first aspect of the present invention relates to a method for modifying melamine derivatives by introducing substituents on the N atom of melamine or an N-substituted melamine derivative, characterized by heating melamine or an N-substituted melamine derivative and an alcohol in the presence of a mixed catalyst comprising a hydrogenation catalyst and a dehydrogenation catalyst, and hydrogen to allow reaction.

A second aspect of the present invention relates to a method for modifying melamine derivatives by introducing a substituent on the N atom of melamine or an N-substituted melamine derivative, characterized by heating melamine or an N-substituted melamine derivative and an alcohol in the presence of a hydrogenation catalyst and hydrogen with addition/coexistence of a metal to allow reaction.

The N-substituted melamine derivatives obtained by the modification method of the present invention, which the method involves incorporation of a substituent group to the amino group on a triazine ring carbon atom of melamine, are useful compound groups that are used widely as various fine chemical intermediates for agricultural chemicals, medicines, dyes, paints and the like, as forming components for various resin materials, in particular an aminoplast, and as a flame retardant.

BACKGROUND ART

From the interest on substituted triazines as materials for various resin and fine chemicals, various synthetic methods and derivatives thereof have been developed.

As the synthetic method, for example, reported are various novel synthetic methods for catalytically obtaining N-substituted triazine derivatives using industrial starting materials, such as the synthetic method by amino exchange reaction between melamine and a corresponding amine derivative [as described in U.S. Pat. No. 4,618,676 (1986), U.S. Pat. No. 4,668,785 (1987), etc.], the method for obtaining an N-substituted triazine derivative using a 1,3,5-triazine derivative, typically represented by melamine, as a starting material and an alcohol [WO95/03287 (corresponding to JP-A Hei8-27128)], the method for obtaining N-substituted triazine derivatives using an aldehyde and a ketone [WO95/30662 (corresponding to JP-A Hei8-193071)], and the method for obtaining N-substituted triazine derivatives using an olefin (JP-A Hei8-27125), proposed by the present inventors. Also, reported are the method for obtaining N-substituted triazine derivatives proposed by the present inventors by reacting a 1,3,5-triazine derivative as a starting material with an alcohol in the presence of a metal catalyst and hydrogen [as described in WO97/24338 (corresponding to JP-A Hei10-231291), etc.]

The methods described in U.S. Pat. Nos. 4,618,676 (1986) and 4,668,785 (1987) and the like perform reactions at elevated temperatures using acid catalysts and are extremely excellent methods for introducing general alkyl groups or a hydroxyethyl group. However, as for amines, generally those that are available at low costs are limited so that there is a limitation on the starting material for introducing various substituents according to this method, resulting in that only limited compounds can be industrially supplied at low costs.

The above-described production methods by the present inventors are methods using starting materials that can be available at low costs on an industrial scale. In particular, those methods using alcohols are recommendable methods from the viewpoints of the kind, price, stability and the like of the starting material. However, sometimes a high temperature and a long time are required depending on the reactivity of the substance and there may occur problems, such as induction of side reactions that will not be observed usually and low productivity.

Therefore, it has now been desired to develop a method for modifying melamine derivatives that can use alcohols that can be available at low costs on an industrial scale and is further improved industrially.

DISCLOSURE OF THE INVENTION

As a result of intensive investigation by the present inventors to solve the above production methods, in a first invention, the present invention having practically applicable reactivity and productivity and being widely applicable to various alcohols has been completed, in which a melamine derivative and an industrially inexpensive alcohol are reacted in the presence of a mixed catalyst comprising a hydrogenation catalyst and a dehydrogenation catalyst, and hydrogen gas to introduce a substituent on the amino group of the melamine derivative.

In a second invention, the present invention having practically applicable reactivity and productivity and being widely applicable to various alcohols has been completed, in which a melamine derivative and an industrially inexpensive alcohol are reacted in the presence of a hydrogenation catalyst and hydrogen, with addition/coexistence of a selected metal to introduce a substituent group on the amino group of the melamine derivative.

The N-substituted melamine derivatives obtained by the present reaction inhibit the association of multiple molecules by hydrogen bonds between the molecules that is inherent to melamine so that the products generally have improved solubility in water and/or various polar solvents as compared with the starting material melamine, and at the same time have improved compatibility with other organic compounds due to decreased melting points. These changes in physical properties further improve the reactivity with other reactive compounds considerably. Hence, said melamine derivative can be applied to those resins for which it has conventionally been difficult to use melamine, and at the same time exhibit very great modification effects.

An object of the present invention is to provide a method for modifying melamine derivatives that enable to easily produce N-substituted melamine derivatives that can be used widely as fine chemical intermediates such as various agricultural chemicals, medicines, dyes and paints, as various resin materials and as flame retardant materials.

In the first aspect, the present invention relates to a method for modifying melamine derivatives by introducing a substituent to melamine or an N-substituted melamine derivative, characterized by heating melamine or an N-substituted melamine derivative and an alcohol in the presence of a mixed catalyst comprising a hydrogenation catalyst and a dehydrogenation catalyst, and hydrogen to allow reaction.

In the second aspect, the present application relates to a method for modifying melamine derivatives by introducing a substituent to melamine or the N-substituted melamine derivative, characterized by heating melamine or an N-substituted melamine derivative and an alcohol in the presence of a hydrogenation catalyst and hydrogen with addition/coexistence of a selected metal to allow reaction.

Hereinafter, the first and second inventions will be described in more detail.

Melamine or N-substituted melamine derivatives, the starting materials of the present invention, are melamine derivatives represented by the general formula (I)

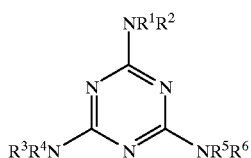

(I)

wherein at least one of groups $R^1$, $R^2$, $R^3$, $R^4$, $R^5$ and $R^6$ is a hydrogen atom, and other groups each independently are $C_{1-20}$ alkyl group (the alkyl may optionally be substituted by one or more substituents, which are different or the same, selected from the group consisting of halogen, $C_{1-6}$ alkoxy, $C_{2-6}$ dialkylamino, $C_{2-7}$ alkoxycarbonyl and phenyl.) or phenyl (the phenyl may optionally be substituted by one or more substituents, which are different or the same, selected from the group consisting of halogen, $C_{1-6}$ alkyl, $C_{1-6}$ alkoxy and $C_{1-6}$ haloalkyl.), or two groups on the same nitrogen atom may combine to form a 3- to 6-membered nitrogen-containing cyclic structure composed of different atoms optionally selected from the group consisting of a carbon atom, an oxygen atom and a nitrogen atom.

Among these, the melamine derivatives that are used more preferably as a starting material are those melamine derivatives of the general formula (I) in which at least one of groups $R^1$, $R^2$, $R^3$, $R^4$, $R^5$ and $R^6$ is a hydrogen atom, and other groups each independently are $C_{1-20}$ alkyl group (the alkyl may be substituted by one or more substituents, which are different or the same, selected from the group consisting of halogen, $C_{1-6}$ alkoxy and phenyl.) or phenyl (the phenyl may optionally be substituted by one or more substituents, which are different or the same, selected from the group consisting of halogen and $C_{1-6}$ alkyl.), or two groups on the same nitrogen atom may combine to form a 3- to 6-membered nitrogen-containing cyclic structure composed of different atoms optionally selected from the group consisting of a carbon atom, an oxygen atom and a nitrogen atom.

Further, in the melamine derivatives of the general formula (I), those melamine derivatives in which at least one of groups $R^1$, $R^2$, $R^3$, $R^4$, $R^5$ and $R^6$ is a hydrogen atom, and the other groups each independently are $C_{1-20}$ alkyl group or a phenyl group, or two groups on the same nitrogen atom may combine to form a 3- to 6-membered nitrogen-containing cyclic structure composed of different atoms optionally selected from the group consisting of a carbon atom and a nitrogen atom are desirable as more preferable ones upon use. In particular, in industry, melamine is the most preferable as the starting material because of its price and amount of supply.

As described above, in the present reaction, it is possible to provide all the melamine derivatives that have substituent groups that do not directly participate in the reaction. The starting material that is easily available in industry includes melamine and various melamine derivatives (these are available mainly as a main component of thermosetting resins or a modifier, crosslinking agent for baking paints, and their synthesis method is described in detail in "s-Triazines and derivatives. The Chemistry of Heterocyclic Compounds", E. M. Smolin and L. Rapoport, Interscience Publishers Inc., New York, 1959.).

The alcohols that can be used in the present invention are alcohols of the general formula (II)

R—OH (II)

wherein R is $C_{1-20}$ alkyl (the alkyl may optionally be substituted by one or more substituents, which are different or the same, selected from the group consisting of a halogen atom, hydroxyl, carboxyl, $C_{1-6}$ alkoxy, $C_{1-6}$ hydroxyalkoxy, $C_{2-10}$ alkoxyalkoxy, $C_{2-10}$ hydroxyalkoxyalkoxy, $C_{2-6}$ alkoxycarbonyl, $C_{2-10}$ dialkylamino and phenyl.).

Further, in the alcohol of the general formula (II), those alcohols in which R is $C_{1-20}$ alkyl group (the alkyl may optionally be substituted by one or more substituents, which are different or the same, selected from the group consisting of hydroxyl, $C_{1-6}$ alkoxy, $C_{1-6}$ hydroxyalkoxy, $C_{2-10}$ hydroxyalkoxyalkoxy, $C_{2-6}$ alkoxycarbonyl and a phenyl.) are used more preferably, and many alcohols that are available in industry can be used as a starting material without a problem.

Among these, typical examples of alcohols that are easily available industrially include methanol, ethanol, n-propanol, isopropanol, n-butanol, sec-butanol, iso-butanol, tert-butanol, 1-pentanol, isoamyl alcohol, neopentyl alcohol, n-hexanol, 2-ethylbutanol, methylamyl alcohol, cyclohexanol, n-octanol, 2-ethylhexanol, cyclohexylmethanol, n-nonanol, n-decanol, n-dodecanol, n-hexadecanol, n-octadecanol, ethylene chlorohydrin, ethylene bromohydrin, propylene chlorohydrin, propylene bromohydrin, ethylene glycol, 1,2-propylene glycol, 1,3-propylene glycol, 2,2-dimethyl-1,3-propanediol, 1,4-butanediol, 1,5-pentanediol, 1,6-hexanediol, 1,9-nonanediol, methyl cellosolve, ethyl cellosolve, isopropyl cellosolve, butyl cellosolve, methoxy propylene glycol, ethoxy propylene glycol, butoxy propylene glycol, 3-methoxy-l-butanol, methoxy ethoxy ethanol, ethoxy ethoxy ethanol, diethylene glycol, triethylene glycol, dipropylene glycol, glycolic acid, methyl glycolate, ethyl glycolate, tert-butyl glycolate, dimethylaminoethanol, diethylaminoethanol, benzyl alcohol, 1-phenethyl alcohol, 2-phenethyl alcohol and the like.

The amount of use of the above-described alcohols may be in any range depending on the purpose. Generally, the range of from 0.01 to 500 times moles, practically from 0.1 to 50 times moles based on mole of the melamine derivative as a starting material is effective in view of reactivity and handling property. When excess amounts of alcohols are used, the alcohols can serve as reaction solvents as well in operation.

The difference between the first and second inventions is a difference in catalyst system to be used in the reaction. In the first invention, a catalyst system comprising a hydrogenation catalyst and a dehydrogenation catalyst is used. In the second invention, a catalyst system comprising a hydrogenation catalyst and a selected metal is used. In these catalyst systems, the present invention is distinguished from the conventional method using a metal catalyst in the reaction.

Hereinafter, description will be made of the catalyst system used in the first invention (hydrogenation catalyst-dehydrogenation catalyst).

The hydrogenation catalysts used in the reaction of the first invention are catalysts that contain one or more metals selected from the group consisting of iron, cobalt, nickel, copper, ruthenium, rhodium, palladium, iridium and platinum, and have hydrogenation activity in a hydrogen gas atmosphere. Among these preferred are those catalysts that contain one or more metals selected from the group consisting of cobalt, nickel, ruthenium, rhodium, palladium and platinum.

In particular, taking the activity in the reaction and the industrial economy into consideration, catalysts that contain one or more metals selected from the group consisting of nickel, ruthenium, rhodium and palladium are preferred.

The dehydrogenation catalysts used in the reaction of the first invention are those catalysts that contain one or more metals selected from the group consisting of copper, zinc, iron, molybdenum, chromium, nickel, ruthenium and barium and oxide thereof as a major component, and have oxidation dehydrogenation activity. In particular, taking economy and dehydrogenation activity into consideration, catalysts that contain one or more metals selected from the group consisting of copper, zinc, iron, chromium, nickel and barium and oxide thereof are preferred.

In the above-described catalysts, the hydrogenation catalyst can function as a dehydrogenation catalyst in the absence of hydrogen. Also, the dehydrogenation catalyst can function as a hydrogenation catalyst in hydrogen pressurized atmosphere. However, the present invention achieves very high reactivity as compared with the case where they are used singly due to the synergism between both catalysts, and hence both catalysts are classified by their general functions for convenience's sake.

In the present reaction, it is preferred to perform the reaction in a non-uniform system since the catalyst is a mixed catalyst system, so that usually the above metal catalyst is provided preferably in the form of a solid catalyst. In practice, good results can be obtained when either a fluidized bed or a fixed bed is used.

In the case of the hydrogenation catalyst, it is practically desirable to use a carried catalyst of a metal used preferably, such as nickel, ruthenium, rhodium or palladium. In this case, as the carrier, crystal or amorphous oxides of silicon or aluminum such as silica, alumina, aluminosilicate, silica-alumina, zeolite, diatomaceous earth and clay mineral, inorganic salts such as calcium carbonate, barium carbonate and barium sulfate, or activated carbon are generally industrially preferred.

The dehydrogenation catalysts are preferably oxides of metals that exhibit good activity, such as iron, copper, zinc, chromium, nickel and barium. These can be used in combination with each other or with other carriers such as silica and alumina. In particular, to give suitable activity for the reaction, the metal oxide is often used as a multi-component catalyst. For example, it is preferably to use as a metal oxide-mixed system or as a mixed metal oxide, such as $CuO$—$Cr_2O_3$, $CuO$—$Cr_2O_3$—$BaO$, $CuO$—$Cr_2O_3$—$NiO$—$BaO$, $ZnO$—$Cr_2O_3$, $ZnCr_2O_4$, $ZnFe_2O_4$, $Ni/NiO$—$SiO_2/Al_2O_3$, and $Ni/NiO$—$ZrO_2/SiO_2$.

In addition to the above metals, other trace metal components can be added to increase the activity of the catalyst, stabilize the catalyst, or prevent the deterioration or deactivation of the catalyst.

The each amount of use of the above hydrogenation catalyst and dehydrogenation catalyst is in the range of usually 0.00001 to 200 mole %, preferably 0.0001 to 100 mole %, based on the melamine derivative of the general formula (I). The mixing ratio that shows a preferable reactivity is obtained from the above range to use.

It is sometimes preferable that the reaction is performed with addition of additives, if needed. The additive includes, for example, monodentate or multidentate tertiary phosphines, phosphorous acid esters, phosphonium salts, phosphoric acid esters, and the like.

The amount of use of additives may be in the range of usually 0.01 to 10,000 mole %, preferably 1 to 5,000 mole %, based on the metal catalyst.

The catalyst system used in the second invention (hydrogenation catalyst-metal) will be described below.

The hydrogenation catalysts used in the reaction of the second invention are those catalysts that contain one or more metals selected from the group consisting of nickel, copper, ruthenium, rhodium, palladium, iridium and platinum, and have hydrogenation activity in a hydrogen gas atmosphere. Among them preferred are those catalysts that contain one or more metals selected from the group consisting of nickel, ruthenium, palladium and platinum.

In particular, taking activity in the reaction and industrial economy into consideration, a catalyst that contains palladium is preferred. Taking the form of use into consideration, it is practically preferred to use a carried catalyst. In this case, the carrier, which can be used, includes crystal or amorphous oxides of silicon or aluminum such as silica, alumina, aluminosilicate, silica-alumina, zeolite, diatomaceous earth and clay mineral, inorganic salts such as calcium carbonate, barium carbonate and barium sulfate, or activated carbon. In particular, a catalyst that contains palladium carried on activated carbon is most preferred.

The amount of use of the above hydrogenation catalyst is in the range of usually 0.00001 to 20 mole %, preferably 0.0001 to 10 mole %, based on the mole of the melamine derivative of the general formula (I). The mixing ratio that shows a preferable reactivity is obtained from the above range to use.

It is sometimes preferable that the reaction is performed with addition of additives, if needed. The additive includes, for example, monodentate or multidentate tertiary phosphines, phosphorous acid esters, phosphonium salts, phosphoric acid esters, and the like.

The amount of use of additives may be in the range of usually 0.01 to 10,000 mole %, preferably 1 to 5,000 mole %, based on the metal catalyst.

The metals to be added and allowed to coexist in the reaction are preferably those that contains one or more metals selected from the group consisting of iron, cobalt and manganese as a major component. In particular, taking productivity, economy and versatility into consideration, one or two of the metals selected from iron and cobalt are preferred.

The above metals exhibit the effect of promoting the reaction so far as it has a surface area greater than a predetermined level to the reaction system. Therefore, it may be processed in any way so far as it satisfies the condition in shape. The metals in the form of plates having fine protrusions or cavities, particles, or fine particles having a large surface area can be used without any problem.

In laboratory, metals in the form of fine particles are preferred. However, in industry, it is preferred to use a reactor filled with a metal processed so as to have desired function.

In the first and second inventions, the reaction temperature for performing the present reaction can be usually 100 to 500° C. Taking the boiling point of alcohol to be used, reactivity, reaction rate, productivity, practical application and the like into consideration, it is preferably 150 to 300° C.

It is desirable that the reaction conditions is selected so that the reaction time can be set usually to 1 to 100 hours, preferably to 1 to 20 hours, depending on the reactivity of the melamine derivative of the general formula (I).

The present reaction can proceed without solvents. It is possible to use solvents, if needed, in view of handling property and the like.

As for the solvent, there is not particular limitation so far as it is inactive to the reaction. The solvent includes, for example, ethers such as tetrahydrofuran, diethyl ether, dimethoxymethane, dimethoxyethane, diethoxymethane, diethoxyethane, ethylene glycol dimethyl ether, ethylene glycol diethyl ether, ethylene glycol dibutyl ether, diethylene glycol diethyl ether and 1,4-dioxane, aromatic hydrocarbons such as benzene, toluene, xylene, mesitylene, cumene, chlorobenzene, o-dichlorobenzene, m-dichlorobenzene, p-dichlorobenzene and tetrahydronaphthalene, aliphatic hydrocarbons such as pentane, hexane, cyclohexane, heptane, octane and decane, nitriles such as acetonitrile and propionitrile, esters such as methyl acetate, ethyl acetate, butyl acetate, ethyl propionate, methyl benzoate and ethyl benzoate, amides such as N,N-dimethylformamide, N,N-dimethylacetamide and N-methylpyrrolidone, 1,3-dimethylimidazolidinone, urea such as N,N,N',N'-tetramethylurea, and water. These may be used singly or in combination with each other.

The alcohol of the general formula (II) in excess amount may be used as a solvent.

The present reaction can proceed in an inert gas atmosphere. However, since the dehydrogenation reaction of the starting material such as alcohol, hydrogenation such as reductive alkylation and the like consists of reactions relating to donation and reception of hydrogen, performing the reaction in a reductive atmosphere by having hydrogen existing in the reaction system gives preferable results.

As means for having hydrogen existing in the reaction system, a method in which the reaction per se is performed in hydrogen gas or in a gas atmosphere that contains hydrogen is desirable as a simple method.

When hydrogen gas or a gas containing hydrogen is used, the partial pressure of such hydrogen is preferably 0.01 to 500 kg/cm$^2$, and industrially the pressure of 0.1 to 200 kg/cm$^2$ is practically preferred. In the case of the gas containing hydrogen, various gasses may be used as a diluent gas so far as they do not participate in the reaction. For example, inert gasses such as nitrogen, argon, and helium are generally used. Carbon monoxide, carbon dioxide, ammonia gas, air, etc. may also be used for the purpose of stabilization of products and catalysts. When these mixed gases are used, there is no problem if the hydrogen partial pressure sufficient for the reaction is present. It is desirable that the total pressure of the mixed gas be in the range of 0.1 to 500 kg/cm$^2$, preferably 0.5 to 300 kg/cm$^2$.

When the present reaction is performed at the elevated temperature, the autogenous pressures generated by alcohols, solvents and the like occur. It is desirable from the viewpoint of apparatus and practical operation that the total pressure of the reaction system is set at 300 kg/cm$^2$ or less inclusive of the autogenous pressures.

In the treating method after completion of the reaction, the solvent is removed by evaporation or the like if necessary, and at this stage unreacted melamine or the like may be crystallized to remove, or the product can be extracted and separated by a combination of an organic solvent-water or the like. If necessary, the reaction product can easily be made highly pure, purified and isolated by recrystallization, distillation, chromatographic separation, salt formation and the like. The metal catalyst can be separated and recovered by filtration or the like and can be reused if necessary.

In the present reaction, to give highly modified compounds sequentially along with the number of reactive amino groups and substituted amino groups on the melamine derivative, their reactivity, or the reaction proceeding, generally several kinds of products are obtained in the form of a mixture and its composition can be controlled to some extent through the reaction conditions or the like.

Depending on the situation in which the resulting melamine derivative is used, the product of the production method of the present invention can be provided per se as mixture, or if necessary, it can be separated/divided to used as highly pure or completely pure substance by the above generally used post-treatment methods.

The N-substituted melamine derivatives obtained by the method for modifying the amino groups on melamine or the N-substituted melamine derivatives according to the present invention are melamine derivatives of the general formula (III)

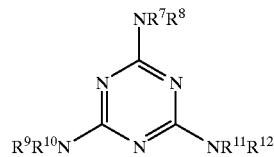

(III)

wherein at least one of groups $R^7$, $R^8$, $R^9$, $R^{10}$, $R^{11}$ and $R^{12}$ is a substituent R (R is $C_{1-20}$ alkyl (the alkyl may optionally be substituted by one or more substituents, which are different or the same, selected from the group consisting of halogen, hydroxyl, carboxyl, $C_{1-6}$ alkoxy, $C_{1-6}$ hydroxyalkoxy, $C_{2-10}$ alkoxyalkoxy, $C_{2-10}$ hydroxyalkoxyalkoxy, $C_{2-6}$ alkoxycarbonyl, $C_{2-10}$ dialkylamino and phenyl.).), and other groups each independently are hydrogen, $C_{1-20}$ alkyl (the alkyl may optionally be substituted by one or more substituents, which are different or the same, selected from the group consisting of halogen, $C_{1-6}$ alkoxy, $C_{2-6}$ dialkylamino, $C_{2-7}$ alkoxycarbonyl and phenyl.) or phenyl group (the phenyl may optionally be substituted by one or more substituents, which are different or the same, selected from the group consisting of halogen, $C_{1-6}$ alkyl, $C_{1-6}$ alkoxy and $C_{1-6}$ haloalkyl.), or two groups on the same nitrogen atom may combine to form a 3- to 6-membered nitrogen-containing cyclic structure composed of different atoms optionally selected from the group consisting of a carbon atom, an oxygen atom and a nitrogen atom.

Among them, the melamine derivatives that can be produced preferably are those melamine derivatives of the general formula (III) in which at least one of groups $R^7$, $R^8$, $R^9$, $R^{10}$, $R^{11}$ and $R^{12}$ is a substituent R (R is $C_{1-20}$ alkyl (the alkyl may optionally be substituted by one or more substituents, which are different or the same, selected from the group consisting of halogen, hydroxyl, carboxyl, $C_{1-6}$ alkoxy, $C_{1-6}$ hydroxyalkoxy, $C_{2-10}$ alkoxyalkoxy, $C_{2-10}$ hydroxyalkoxyalkoxy, $C_{2-6}$ alkoxycarbonyl, $C_{2-10}$ dialkylamino and phenyl.).), and other groups each independently are hydrogen atom, $C_{1-20}$ alkyl (the alkyl may optionally be substituted by one or more substituents, which are different or the same, selected from the group consisting of halogen, $C_{1-6}$ alkoxy and phenyl.) or phenyl (the phenyl may optionally be substituted by one or more substituents, which are different or the same, selected from the group consisting of halogen and $C_{1-6}$ alkyl.), or two groups on the same nitrogen atom may combine to form a 3- to 6-membered nitrogen-containing cyclic structure composed of different atoms optionally selected from the group consisting of a carbon atom, an oxygen atom and a nitrogen atom.

Further, the melamine derivatives that can be produced more preferably industrially are those melamine derivatives of the general formula (III) in which at least one of groups $R^7$, $R^8$, $R^9$, $R^{10}$, $R^{11}$ and $R^{12}$ is a substituent R (R is $C_{1-20}$ alkyl (the alkyl may optionally be substituted by one or more substituents, which are different or the same, selected from the group consisting of halogen, hydroxyl, carboxyl, $C_{1-6}$ alkoxy, $C_{1-6}$ hydroxyalkoxy, $C_{2-10}$ alkoxyalkoxy, $C_{2-10}$ hydroxyalkoxyalkyl, $C_{2-6}$ alkoxycarbonyl, $C_{2-10}$ dialkylamino and phenyl.).), and other groups each independently are hydrogen, $C_{1-20}$ alkyl or phenyl, or two groups on the same nitrogen atom may combine to form a 3- to 6-membered nitrogen-containing cyclic structure composed of different atoms optionally selected from the group consisting of a carbon atom and a nitrogen atom.

In particular, taking easiness of availability and price of starting materials into consideration, the melamine derivatives that are most suitable for the purpose of the present invention are those melamine derivatives of the general formula (III) which can be prepared in one step from melamine, and in which at least one of groups $R^7$, $R^8$, $R^9$, $R^{10}$, $R^{11}$ and $R^{12}$ is a substituent R (R is $C_{1-20}$ alkyl (the alkyl may optionally be substituted by one or more substituents, which are different or the same, selected from the group consisting of hydroxyl, $C_{1-6}$ alkoxy, $C_{1-6}$ hydroxyalkoxy, $C_{2-10}$ hydroxyalkoxyalkoxy, $C_{2-6}$ alkoxycarbonyl and phenyl.).), and other groups are hydrogen.

As described above, in the present invention, the melamine derivatives as starting materials include melamine and various melamine derivatives and the alcohols include those alcohols that are available at low costs as various petrochemical products. Combinations of these can provide representative products.

The range of starting materials that can be applied to the present reaction is not limited by the price and easy availability of starting materials. Hereinafter, the scope of the present reaction will be made clearer by indicating specific examples of starting material and substituent of the product in the present reaction.

Of the substituent groups $R^1$, $R^2$, $R^3$, $R^4$, $R^5$ and $R^6$ in the general formula (I) for the starting materials and substituent groups $R^7$, $R^8$, $R^9$, $R^{10}$, $R^{11}$ and $R^{12}$ in the general formula (III) for the products, those other than hydrogen atoms include the followings:

As the $C_{1-20}$ alkyl groups that may have a substituent group include methyl, ethyl, n-propyl, i-propyl, n-butyl, i-butyl, sec-butyl, tert-butyl, n-amyl, i-amyl, neopentyl, n-hexyl, cyclohexyl, cyclohexylmethyl, heptyl, octyl, 2-ethylhexyl, nonyl, decyl, hexadecyl, octadecyl, trifluoromethyl, 3-chloropropyl, 2,2,2-trifluoroethyl, methoxymethyl, methoxyethyl, ethoxymethyl, cyclohexyloxyethyl, N,N-dimethylaminomethyl, N,N-diethylaminomethyl, N,N-diisopropylaminomethyl, N,N-dimethylaminoethyl, N,N-diethylaminoethyl, N,N-diisopropylaminoethyl, methoxycarbonylmethyl, methoxycarbonylethyl, tert-butoxycarbonylmethyl, cyclohexyloxycarbonylmethyl, methoxycarbonylethyl, methoxycarbonylethyl, tert-butoxycarbonylethyl, cyclohexyloxycarbonylethyl, benzyl, 1-phenethyl, 2-phenethyl group and the like.

The phenyl groups that may be substituted include phenyl, 2-chlorophenyl, 4-chlorophenyl, 2-fluorophenyl, 4-fluorophenyl, 2,4-dichlorophenyl, 2-fluoro-4-chlorophenyl, 2,3,4,5,6-pentafluorophenyl, p-tolyl, m-tolyl, o-tolyl, 3,5-dimethylphenyl, 4-cyclohexylphenyl, 2,4,6-trimethylphenyl, 2-methyl-4-isopropylphenyl, 3,5-dimethoxyphenyl, 4-cyclopentyloxyphenyl, 2-trifluoromethylphenyl, 3-trifluoromethylphenyl, a 4-trifluoromethyl and the like.

The groups forming a 3- to 6-membered nitrogen containing cyclic structure composed of different atoms optionally selected from the group consisting of a carbon atom, a oxygen atom and a nitrogen atom by combination of two groups on the same nitrogen atom include aziridino, azetidino, pyrrolidino, piperidino, morpholino and the like.

The groups forming a 3- to 6-membered nitrogen containing cyclic structure composed of different atoms optionally selected from the group consisting of a carbon atom and a nitrogen by combination of two groups on the same nitrogen atom include aziridino, azetidino, pyrrolidino, piperidino and the like.

Examples of the substituent groups that are introduced after the reaction include methyl, ethyl, n-propyl, i-propyl, n-butyl, i-butyl, a sec-butyl, tert-butyl, n-amyl, i-amyl, neopentyl, n-hexyl, cyclohexyl, cyclohexylmethyl, heptyl, octyl, 2-ethylhexyl, nonyl, decyl, hexadecyl, octadecyl, trifluoromethyl, 2-chloropropyl, 3-chloropropyl, 2-bromopropyl, 2,2,2-trifluoroethyl, hydroxyethyl, 2-hydroxypropyl, 3-hydroxypropyl, 3-hydroxy-2,2-dimethylpropyl, 1-methyl-2-hydroxypropyl, 4-hydroxybutyl, 5-hydroxypentyl, 6-hydroxyhexyl, 9-hydroxynonyl, 12-hydroxydodecyl, carboxymethyl, 2-carboxyethyl, 2-carboxypropyl, methoxymethyl, methoxyethyl, ethoxymethyl, isopropoxyethyl, butoxyethyl, cyclohexyloxyethyl, 5-hydroxy-3-oxapentyl, 5-hydroxy-3-oxa-2,5-diemthylpentyl, 8-hydroxy-3,6-dioxaoctyl, methoxyethoxyethyl, ethoxyethoxyethyl, methoxycarbonylmethyl, methoxycarbonylmethyl, tert-butoxycarbonylmethyl, cyclohexyloxycarbonylmethyl, methoxycarbonylethyl, methoxycarbonylethyl, tert-butoxycarbonylethyl, cyclohexyloxycarbonylethyl, N,N-dimethylaminomethyl, N,N-diethylaminomethyl, N,N-diisopropylaminomethyl, N,N-dimethylaminoethyl, N,N-diethylaminoethyl, N,N-diisopropylaminoethyl, benzyl, 1-phenethyl, 2-phenethyl and the like.

These substituent groups are only typical examples and the present invention should not be construed as being limited thereto.

BEST MODE FOR CARRYING OUT THE INVENTION

Hereinafter, the present invention will be described in more detail by examples. However, the present invention should not be construed as being limited thereto.

In the present examples, products were independently prepared as reference standard [the synthesis was performed according to J. Am. Chem. Soc., Vol. 73, p.2984 (1951), JP-A Hei3-215564 and U.S. Pat. No. 4,886,882], and calibration curves were prepared using the products isolated as pure preparations and internal standard substances. The amounts of respective products in the reaction products were determined accurately by the internal standard quantitative method using high performance liquid chromatography.

The analytical conditions used for the high performance liquid chromatography were as shown below.
[Standard analytical conditions used in quantitative analysis] (Gradient analysis)
Eluant:
   Acetonitrile/$H_2O$=5:95
      Eluted with an eluant of this composition for 10 minutes.

Acetonitrile/H$_2$O=5:95
↓ Gradient eluted for 20 minutes.
Acetonitrile/H$_2$O=100:0
Eluted with an eluant of this composition for 10 minutes.
Detection method: UV 230 nm
Column: Inertsil Ph 150 mm×4.6 mmφ, manufactured by GL Science.
Flow rate: 1.0 ml/min
Temperature for analysis: 40° C.
Internal standard substance: Diethyl phthalate or dipropyl phthalate Reference Example 1

Synthesis of 2,4-diamino-6-chloro-1,3,5-triazine

To a solution of 184.5 g (1.0 mol) of cyanuric chloride dissolved in 800 ml of acetonitrile at room temperature and cooled to 0° C., 303.7 g (5.0) of 28% aqueous ammonia solution was added at dropwise over 2 hour with vigorous stirring such that the reaction temperature was maintained below 10° C. After completion of the addition, the cooling was stopped and the mixture was stirred at room temperature for 1 hour and then the temperature was gradually elevated to 45° C. and the reaction was continued for additional 4 hours. After cooling, the product was filtered off and further washed with a large amount of water. The filtrate was dried at 50° C. for 6 hours under vacuum to obtain 115 g (yield: 79%) of the titled compound.

Reference Example 2

Synthesis of 2,4-diamino-6-butylamino-1,3,5-triazine

A mixed solution of 14.5 g (0.1 mol) of 2,4-diamino-6-chloro-1,3.5-triazine synthesized in Reference Example 1, 100 ml of water and 29.2 g (0.4 mol) of butylamine was warmed with stirring to the reflux temperature finally at which the reaction was allowed to proceed for 6 hours. After cooling the reaction mixture, the product was filtered off and further sufficiently washed with a large amount of water and then with toluene. the filtrate was dried at 70° C. for 6 hours under vacuum to obtain 17.5 g (yield: 96%) of the titled compound. Melting point: 167° C.

Reference Example 3

Synthesis of 2-amino-4,6-bis (n-butylamino)-1,3,5-triazine

To a mixture of 18.5 g (0.1 mol) of cyanuric chloride and 150 ml of acetonitrile, a mixed solution of 7.3 g (0.1 mol) of n-butylamine and 20 ml of water was added at dropwise over 2 hours such that the reaction temperature did not exceed 5° C. thereafter, a solution of 10.0 g (0.1 mol) of potassium hydrogen carbonate in 40 ml of water was added at dropwise over 1 hour while maintaining the temperature below 5° C. and the stirring was continued for additional 2 hours. Subsequently, 15.2 g (0.25 mol) of 28% aqueous ammonia solution was added at dropwise at the same temperature and the temperature was gradually elevated to 50° C. at which temperature the stirring was continued for 4 hours. Crystals were filtered from the resulting slurry solution, washed sufficiently with water, and then dried to obtain 2-amino-4-n-butylamino-6-chloro-1,3,5-triazine as an intermediate. The total amount of crystals obtained were suspended in 100 ml of water, 8.1 g (0.11 mol) of n-butylamine was added thereto, and then reaction was allowed to proceed at reflux temperature for 2 hours. Thereafter, a solution of 4.0 g (0.1 mol) of sodium hydroxide in 20 ml of water was added at dropwise over 1 hour and then the mixture was cooled and 100 ml of toluene was added thereto to extract the product. Thereafter, the product was washed with 80 ml of water 5 times. Distilling off the solvent from the resulting organic layer under reduced pressure afforded 27.0 g (yield: 92%) of the titled compound. Melting point: 73° C.

Reference Example 4

Synthesis of 2,4,6-tris(butylamino)-1,3,5-triazine

To a solution of 18.5 g (0.1 mol) of cyanuric chloride dissolved in 150 ml of acetonitrile and cooled to 0° C., a solution of 14.6 g (0.2 mol) of butylamine in 20 ml of water was added at dropwise over 1 hour with stirring such that the reaction temperature did not exceed 5° C. While continuing the stirring, a solution of 20.0 g (0.2 mol) of potassium hydrogen carbonate in 100 ml of water was added at dropwise at the same temperature. Thereafter, the reaction temperature was gradually elevated to 45° C., at which temperature the reaction was continued for additional 8 hours. After confirming completion of the conversion to 2,4-bis(butylamino)-6-chloro-1,3,5-triazine by high performance liquid chromatography, the product was cooled and filtered off. The filtrate cake waswashed sufficiently with a large amount of water and then the obtained 2,4-bis (butylamino)-6-chloro-1,3,5-triazine was suspended in 100 ml of water, 29.2 g (0.4 mol) of butylamine was added thereto, and the mixture was further allowed to react for 6 hours under heating at reflux. After cooling, 200 ml of toluene was added and the mixture was vigorously stirred. Then, the water layer was separated. Further, the toluene layer was washed 3 times with 150 ml of water and then toluene was distilled off from the organic layer by heating under reduced pressure to obtain 28.2 g (yield: 96%) of the titled compound. Property: oily substance.

Reference Example 5

Synthesis of 2,4-diamino-6-(5-hydroxypentylamino)-1,3,5-triazine 7.3 g (0.05 mol) of 2,4-diamino-6-chloro-1,3,5-triazine synthesized in Reference Example 1 was suspended in 25 ml of water and 10.5 g (0.1 mol) of 5-amino-l-pentanol was added at dropwise thereto with stirring. After completion of the addition, the reaction temperature was elevated and mixture was allowed to react by heating at reflux for 2 hours. Further, a solution of 2.0 g (0.05 mol) of sodium hydroxide in 10 ml of water was added at dropwise at the same temperature and the stirring was continued for 2 hours. After confirming completion of the conversion to 2,4-diamino-6-(5-hydroxypentylamino)-1,3,5-triazine by high performance liquid chromatography, the mixture was allowed to cool to room temperature. The resulting white precipitate was filtered off, dried and recrystallized from acetonitrile to obtain 6.4 g (yield: 46%) of the titled compound. Property: white solid.

Reference Example 6

Synthesis of 2-amino-4,6-bis(5-hydroxypentylamino)-1,3,5-triazine

To a solution of 9.20 g (0.05 mol) of cyanuric chloride dissolved in 50 ml of acetonitrile and cooled to 0° C., 5.2 g (0.05 mol) of 5-amino-1-pentanol was added at dropwise over 1 hour with stirring such that the reaction temperature did not exceed 5° C. While continuing the stirring, a solution of 5.0 g (0.05 mol) of potassium hydrogen carbonate in 50 ml of water was added at dropwise at the same temperature. Thereafter, the reaction temperature was gradually elevated to 20° C., at which temperature the reaction was continued for additional 1 hour. Then, 10.5 g of a 28% aqueous ammonia solution was added at dropwise at the same temperature and the stirring was continued for 3 hours. After confirming completion of the conversion to 2-amino-4-chloro-6-(5-hydroxypentylamino)-1,3,5-triazine by high performance liquid chromatography, a solution of 2.0 g (0.05 mol) of sodium hydroxide was added at dropwise and the solvent was distilled off at 40° C. or lower. The resulting white solid was suspended in 100 ml of water and 5.2 g (0.05 mol) of 5-amino-1-pentanol was added thereto. The mixture was allowed to react under heating at reflux for 1 hour. Further, after a solution of 2.0 g (0.05 mol ) of sodium hydroxide in 10 ml of water was added at dropwise at the same temperature, the stirring was continued for 3 hours. After confirming completion of the conversion to 2-amino-4,6-bis(5-hydroxypentylamino)-1,3,5-triazine by high performance liquid chromatography, the solvent was distilled off. The insoluble salts were separated with ethanol and isopropanol to obtain 13.0 g (yield: 87%) of the titled compound. To obtain a reference standard having higher purity, the product was purified by high performance liquid chromatography. Property: oily substance.

Reference Example 7

Synthesis of 2,4,6-tris(5-hydroxypentylamino)-1,3,5-triazine

To a solution of 9.20 g (0.05 mol) of cyanuric chloride dissolved in 50 ml of acetonitrile and cooled to 0° C., 10.5 g (0.1 mol) of 5-amino-1-pentanol was added at dropwise over 1 hour with stirring such that the reaction temperature did not exceed 5° C. While continuing the stirring, a solution of 10.0 g (0.1 mol) of potassium hydrogen carbonate in 100 ml of water was added at dropwise at the same temperature. Thereafter, the reaction temperature was gradually elevated to 45° C., at which temperature the reaction was continued for additional 5 hours. After confirming completion of the conversion to 2,4-bis(5-hydroxypentylamino)-6-chloro-1,3, 5-triazine by high performance liquid chromatography, the solvent was distilled off. 2,4-Bis(5-hydroxypentylamino)-6-chloro-1,3,5-triazine was suspended in 100 ml of water, 5.2 g (0.05 mol) of 5-amino-1-pentanol was added thereto, and the mixture was allowed to react under heating at reflux for 2 hours. Then, a solution of 2.0 g (0.05 mol) of sodium hydroxide in 10 ml of water was added at dropwise at the same temperature and then the stirring was continued for 5 hours. After confirming completion of the conversion to 2,4,6-tris(5-hydroxypentylamino)-1,3,5-triazine by high performance liquid chromatography, the solvent was distilled off. The insoluble salts were separated with ethanol and isopropanol to obtain 18.9 g (yield: 98%) of the titled compound. Property: white solid.

Reference Example 8

Synthesis of 2,4-diamino-6-(5-hydroxy-3-oxapentylamino)-1,3,5-triazine 14.5 g (0.1 mol) of 2,4-diamino-6-chloro-1,3,5-triazine and 11.6 g (0.11 mol) of 2-(2-aminoethoxy)ethanol were added to 60 ml of water and the mixture in a state of suspension was heated with stirring and the temperature thereof was elevated to 100° C. After continuing the reaction for 2 hours, a 20 ml of aqueous solution of 4.0 g (0.1 mol) of sodium hydroxide was added at dropwise over 1 hour while maintaining the reaction temperature and the reaction was continued at the same temperature for 3 hours. The obtained homogeneous reaction mixture was cooled gradually and left to stand at room temperature for one night. The crystals precipitated were collected by filtration, washed with a small amount of water, and recrystallized from water to obtain 13.5 g (yield: 62%) of the object compound, 2,4-diamino-6-(5-hydroxy-3-oxapentylamino)-1,3,5-triazine as crystals.

Reference Example 9

Synthesis of 2-amino-4,6-bis(5-hydroxy-3-oxapentylamino)-1,3,5-triazine 18.5 g (0.1 mol) of cyanuric chloride was added to 100 ml of acetonitrile and cooled to 0° C. To this solution, 10.5 g (0.1 mol) of 2-(2-aminoethoxy) ethanol was added at dropwise over 1 hour with stirring such that the reaction temperature did not exceed 5° C. and the mixture was stirred at 5° C. or lower for further 2 hours. Subsequently, a solution of 10.0 g (0.1 mol) of potassium hydrogen carbonate in 70 ml of water was added at dropwise at the same temperature over 2 hours. Then the cooling was stopped and the stirring was continued until room temperature (25° C.) was reached. Thereafter, 24.3 g (0.4 mol) of a 28% aqueous ammonia solution was gradually added. The temperature was elevated to 40 to 45° C., at which temperature the mixture was allowed to react. The reaction mixture was concentrated under reduced pressure at 50° C. or lower to about a half amount. To the obtained mixture, 10.5 g (0.1 mol) of 2,2-amino-ethoxyethanol was added and the mixture was heated to elevate the temperature to 100° C. After continuing the reaction for 2 hours, a solution of 4.0 g (0.1 mol) of sodium hydroxide in 20 ml of water was added at dropwise over 1 hour while maintaining the reaction temperature and the reaction was continued for further 3 hours at the same temperature. The obtained homogeneous reaction mixture was concentrated to dryness under reduced pressure and then 100 ml of ethanol was added thereto, followed by filtration of insoluble substances. After the filtrate was concentrated to dryness, 100 ml of isopropyl alcohol was added thereto and the same operation was performed. The obtained viscous mixture was purified and separated by silica gel column chromatography (eluant: ethyl acetate/ethanol=1/1) to obtain 25.7 g of the object compound, 2-amino-4,6-bis(5-hydroxy-3-oxapentylamino) -1,3, 5-triazine as a viscous product. Yield: 85%.

Reference Example 10

Synthesis of 2,4,6-tris(5-hydroxy-3-oxapentylamino)-1,3, 5-triazine

To a solution of 9.20 g (0.05 mol) of cyanuric chloride in 50 ml of acetonitrile and cooled to 0° C., 10.6 g (0.1 mol) of 2-(2-aminoethoxy) ethanol was added over 1 hour with stirring such that the reaction temperature did not exceed 5° C. While continuing stirring, a solution of 10.0 g (0.1 mol) of potassium hydrogen carbonate in 100 ml of water was added at dropwise at the same temperature. Thereafter, the reaction temperature was gradually elevated to 45° C., at which temperature stirring was continued for 5 hours. After confirming completion of the conversion to 2,4-bis(5-hydroxy-3-oxapentylamino)-6-chloro-1,3,5-triazine by high performance liquid chromatography, the solvent was distilled off. The 2,4-bis(5-hydroxy-3-oxapentylamino) -6-chloro-1,3,5-triazine was suspended in 100 ml of water and 5.3 g (0.05 mol) of 2-(2-aminoethoxy)ethanol was added thereto. The mixture was allowed to react under heating at reflux for 2 hours. A solution of 2.0 g (0.05 mol) of sodium hydroxide in 10 ml of water was added at dropwise at the same temperature, then the stirring was continued for 5 hours. After confirming completion of the conversion to 2,4,6-tris(5-hydroxy-3-oxapentylamino)-1,3, 5-triazine by high performance liquid chromatography, the solvent was distilled off. The insoluble salts were separated with ethanol and isopropanol to obtain 19.0 g (yield: 97%) of the titled compound. Property: white solid.

Hereinafter, examples of the first invention will be described.

EXAMPLE 1

Reaction of melamine and 1-butanol

In a stainless steel autoclave of an inner volume of 70 ml, 1.26 g (0.01 mol) of melamine, 25 mg of 5% Pd—C catalyst (50% hydrated preparation), 25 mg of $CuO$—$Cr_2O_3$—

NiO—BaO catalyst (T-4364, manufactured by Nissan Girdler Catalyst Co., Ltd.), and 30 ml of butanol were charged. After the inside of the reaction system was sufficiently substituted with nitrogen, 40 kg/cm$^2$ of hydrogen gas was introduced. The temperature was elevated while stirring and the reaction was carried out at a reaction temperature of 240° C. for 2 hours. Then the reaction mixture was cooled and the contents were subjected to quantitative analysis. As a result, the conversion rate of the starting material melamine was 41.3% and the obtained product contained 2,4-diamino-6-butylamino-1,3,5-triazine in a yield of 26.4%, 2-amino-4,6-bis(butylamino)-1,3,5-triazine in a yield of 11.6%, and 2,4,6-tris(butylamino)-1,3,5-triazine in a yield of 1.5%, respectively.

EXAMPLE 2

Reaction of melamine and cyclohexanol

In a stainless steel autoclave of an inner volume of 70 ml, 1.26 g (0.01 mol) of melamine, 25 mg of 5% Pd—C catalyst (50% hydrated preparation), 25 mg of CuO—Cr$_2$O$_3$—NiO—BaO catalyst (T-4364, manufactured by Nissan Girdler Catalyst Co., Ltd.), and 30 ml of cyclohexanol were charged. The inside of the reactor was sufficiently substituted with nitrogen, and then with 10 kg/cm$^2$ of hydrogen gas for 5 times. Leaving 10 kg/cm$^2$ of hydrogen in the reactor, the temperature was elevated while stirring and the reaction was carried out at a reaction temperature of 260° C. for 2hours. Then the reaction mixture was cooled and the contents were subjected to quantitative analysis. As a result, the conversion rate of the starting material melamine was 36.2% and the obtained product contained 2,4-diamino-6-cyclohexylamino-1,3,5-triazine in a yield of 21.6%, 2-amino-4,6-bis(cyclohexylamino)-1,3,5-triazine in a yield of 8.8%, and 2,4,6-tris(cyclohexylamino)-1,3,5-triazine in a yield of 3.2%, respectively.

EXAMPLE 3

Reaction of melamine and 1,5-pentanediol

In a stainless steel autoclave of an inner volume of 100 ml, 1.26 g (10 mmol) of melamine, 125 mg of 5% Pd—C catalyst (50% hydrated preparation), 125 mg of CuO—Cr$_2$O$_3$—NiO—BaO catalyst (T-4364, manufactured by Nissan Girdler Catalyst Co., Ltd.), and 30 ml of 1,5-pentanediol were charged. After the inside of the reaction system was sufficiently substituted with nitrogen gas, 10 kg/cm$^2$ of hydrogen gas was introduced under pressure at normal temperature. Then, the temperature was elevated to 260° C., and after the temperature reached 260° C., the reaction was carried out at the same temperature for further 2 hours. After cooling, the reaction mixture was taken out and quantitative analysis of the reaction product was performed under the above analytical conditions. As a result, the conversion rate of the starting material melamine was 78.0% and it was confirmed that there were produced 2,4-diamino-6-(5-hydroxypentylamino)-1,3,5-triazine in a yield of 39.9%, 2-amino-4,6-bis(5-hydroxypentylamino)-1,3,5-triazine in a yield of 26.5%, and 2,4,6-tris(5-hydroxypentylamino)-1,3,5-triazine in a yield of 9.3%, respectively.

EXAMPLE 4

Reaction of melamine and 1,5-pentanediol

In a stainless steel autoclave of an inner volume of 100 ml, 1.26 g (10 mmol) of melamine, 175 mg of 5% Pd—C catalyst (50% hydrated preparation), 75 mg of CuO—Cr$_2$O$_3$—NiO—BaO catalyst (T-4364, manufactured by Nissan Girdler Catalyst Co., Ltd.), and 30 ml of 1,5-pentanediol were charged. After the inside of the reaction system was sufficiently substituted with nitrogen gas, 10 kg/cm$^2$ of hydrogen gas was introduced under pressure at normal temperature. Then, the temperature was elevated while stirring, and after the temperature reached 260° C., the reaction was carried out at the same temperature for further 2 hours. After cooling, the reaction mixture was taken out and quantitative analysis of the reaction product was performed under the above analytical conditions. As a result, the reaction conversion rate of the starting material melamine was 81.0% and it was confirmed that there were produced 2,4-diamino-6-(5-hydroxypentylamino)-1,3,5-triazine in a yield of 37.6%, 2-amino-4,6-bis(5-hydroxypentylamino)-1,3,5-triazine in a yield of 30.1%, and 2,4,6-tris(5-hydroxypentylamino)-1,3,5-triazine in a yield of 9.0%, respectively.

EXAMPLE 5

Reaction of melamine and 1,5-pentanediol

In a stainless steel autoclave of an inner volume of 100 ml, 1.26 g (10 mmol) of melamine, 75 mg of 5% Pd—C catalyst (50% hydrated preparation), 175 mg of CuO—Cr$_2$O$_3$—NiO—BaO catalyst (T-4364, manufactured by Nissan Girdler Catalyst Co., Ltd.), and 30 ml of 1,5-pentanediol were charged. After the inside of the reaction system was sufficiently substituted with nitrogen gas, 10 kg/cm$^2$ of hydrogen gas was introduced under pressure at normal temperature. Then, the temperature was elevated while stirring, and after the temperature reached 260° C., the reaction was carried out at the same temperature for further 2 hours. After cooling, the reaction mixture was taken out and quantitative analysis of the reaction product was performed under the above analytical conditions. As a result, the reaction conversion rate of the starting material melamine was 67.8% and it was confirmed that there were produced 2,4-diamino-6-(5-hydroxypentylamino)-1,3,5-triazine in a yield of 41.1%, 2-amino-4,6-bis(5-hydroxypentylamino)-1,3,5-triazine in a yield of 19.6%, and 2,4,6-tris(5-hydroxypentylamino)-1,3,5-triazine in a yield of 1.3%, respectively.

EXAMPLE 6

Reaction of melamine and 1,4-butanediol

In a stainless steel autoclave of an inner volume of 100 ml, 1.26 g (10 mmol) of melamine, 125 mg of 5% Pd—C catalyst (50% hydrated preparation), 125 mg of CuO—Cr$_2$O$_3$—NiO—BaO catalyst (T-4364, manufactured by Nissan Girdler Catalyst Co., Ltd.), and 30 ml of 1,4-butanediol were charged. After the inside of the reaction system was sufficiently substituted with nitrogen gas, 10 kg/cm$^2$ of hydrogen gas was introduced under pressure at normal temperature. Then, the temperature was elevated while stirring, and after the temperature reached 260° C., the reaction was carried out at the same temperature for further 2 hours. After cooling, the reaction mixture was taken out and quantitative analysis of the reaction product was performed under the above analytical conditions. As a result, the reaction conversion rate of the starting material melamine was 83.0% and it was confirmed that there were produced 2,4-diamino-6-(4-hydroxybutylamino)-1,3,5-triazine in a yield of 41.3%, 2-amino-4,6-bis(4-hydroxybutylamino)-1,3,5-triazine in a yield of 29.3%, and 2,4,6-tris(4-hydroxybutylamino)-1,3,5-triazine in a yield of 8.2%, respectively.

EXAMPLE 7

Reaction of melamine and 1,4-butanediol

In a stainless steel autoclave of an inner volume of 100 ml, 1.26 g (10 mmol) of melamine, 125 mg of 5% Pd—C catalyst (50% hydrated preparation), 125 mg of CuO—$Cr_2O_3$ catalyst (G13, manufactured by Nissan Girdler Catalyst Co., Ltd.), and 30 ml of 1,4-butanediol were charged. After the inside of the reaction system was sufficiently substituted with nitrogen gas, 10 kg/cm$^2$ of hydrogen gas was introduced under pressure at normal temperature. Then, the temperature was elevated while stirring, and after the temperature reached 260° C., the reaction was carried out at the same temperature for further 2 hours. After cooling, the reaction mixture was taken out and quantitative analysis of the reaction product was performed under the above analytical conditions. As a result, the reaction conversion rate of the starting material melamine was 73.8% and it was confirmed that there were produced 2,4-diamino-6-(4-hydroxybutylamino)-1,3,5-triazine in a yield of 35.2%, 2-amino-4,6-bis(4-hydroxybutylamino)-1,3,5-triazine in a yield of 17.6%, and 2,4,6-tris(4-hydroxybutylamino)-1,3,5-triazine in a yield of 9.8%, respectively.

EXAMPLE 8

Reaction of melamine and 1,3-propanediol

In a stainless steel autoclave of an inner volume of 100 ml, 1.26 g (10 mmol) of melamine, 125 mg of 5% Pd—C catalyst (50% hydrated preparation), 125 mg of CuO—$Cr_2O_3$—NiO—BaO catalyst (T-4364, manufactured by Nissan Girdler Catalyst Co., Ltd.), and 30 ml of 1,3-propanediol were charged. After the inside of the reaction system was sufficiently substituted with nitrogen gas, 10 kg/cm$^2$ of hydrogen gas was introduced under pressure at normal temperature. Then, the temperature was elevated while stirring, and after the temperature reached 260° C., the reaction was carried out at the same temperature for further 2 hours. After cooling, the reaction mixture was taken out and quantitative analysis of the reaction product was performed under the above analytical conditions. As a result, the conversion rate of starting material melamine was 76.5% and it was confirmed that there were produced 2,4-diamino-6-(3-hydroxypropylamino)-1,3,5-triazine in a yield of 37.4%, 2-amino-4, 6-bis(3-hydroxypropylamino)-1,3,5-triazine in a yield of 26.7%, and 2,4,6-tris(3-hydroxypropylamino)-1,3,5-triazine in a yield of 8.9%, respectively.

EXAMPLE 9

Reaction of melamine and diethylene glycol

In a stainless steel autoclave of an inner volume of 100 ml, 1.26 g (10 mmol) of melamine, 250 mg of 5% Pd—C catalyst (50% hydrated preparation), 250 mg of CuO—$Cr_2O_3$—NiO—BaO catalyst (T-4364, manufactured by Nissan Girdler Catalyst Co., Ltd.), and 30 ml of diethylene glycol were charged. After the inside of the system was sufficiently substituted with nitrogen gas, 10 kg/cm$^2$ of hydrogen gas was introduced at normal temperature under pressure. Then, the temperature was elevated while stirring, and after the temperature reached 260° C., the reaction was carried out at the same temperature for further 2 hours. After cooling, the reaction mixture was taken out and quantitative analysis of the reaction product was performed under the above analytical conditions. As a result, the reaction conversion rate of the starting material melamine was 50.0% and it was confirmed that there were produced 2,4-diamino-6-(5-hydroxy-3-oxapentylamino)-1,3,5-triazine in a yield of 34.3% and 2-amino-4,6-bis(5-hydroxy-3-oxapentylamino)-1,3,5-triazine in a yield of 6.7%, respectively.

EXAMPLE 10

Reaction of melamine and diethylene glycol

In a stainless steel autoclave of an inner volume of 100 ml, 1.26 g (10 mmol) of melamine, 250 mg of 5% Pd—C catalyst, 250 mg of CuO and 30 ml of diethylene glycol were charged. After the inside of the reaction system was sufficiently substituted with nitrogen gas, 10 kg/cm$^2$ of hydrogen gas was introduced under pressure at normal temperature. Then, the temperature was elevated while stirring, and after the temperature reached 260° C., the reaction was carried out at the same temperature for further 2 hours. After cooling, the reaction mixture was taken out and quantitative analysis of the reaction product was performed under the above analytical conditions. As a result, the reaction conversion rate of the starting material melamine was 38.8% and it was confirmed that there were produced 2,4-diamino-6-(5-hydroxy-3-oxapentylamino)-1,3,5-triazine in a yield of 22.9% and 2-amino-4,6-bis(5-hydroxy-3-oxapentylamino)-1,3,5-triazine in a yield of 3.9%, respectively.

EXAMPLE 11

Reaction of melamine and 1,4-butanediol

In a stainless steel autoclave of an inner volume of 100 ml, 1.26 g (10 mmol) of melamine, 250 mg of 5% Pd—C catalyst (50% hydrated preparation), 250 mg of Ni/NiO—$SiO_2/Al_2O_3$ catalyst (G-96D, manufactured by Nissan Girdler Catalyst Co., Ltd.), and 30 ml of 1,4-butanediol were charged. After the inside of the reaction system was sufficiently substituted with nitrogen gas, 10 kg/cm$^2$ of hydrogen gas was introduced under pressure at normal temperature. Then, the temperature was elevated while stirring, and after the temperature reached 240° C., the reaction was carried out at the same temperature for further 2 hours. After cooling, the reaction mixture was taken out and quantitative analysis of the reaction product was performed under the above analytical conditions. As a result, the conversion rate of starting material melamine was 89.3% and it was confirmed that there were produced 2,4-diamino-6-(4-hydroxybutylamino)-1,3,5-triazine in a yield of 33.3%, 2-amino-4,6-bis(4-hydroxybutylamino)-1,3,5-triazine in a yield of 36.4%, and 2,4,6-tris(4-hydroxybutylamino)-1,3,5-triazine in a yield of 9.5%, respectively.

EXAMPLE 12

Reaction of melamine and 1,4-butanediol

In a stainless steel autoclave of an inner volume of 100 ml, 3.78 g (30 mmol) of melamine, 250 mg of 5% Pd—C catalyst (50% hydrated preparation), 250 mg of Ni/NiO—$SiO_2/Al_2O_3$ catalyst (G-96D, manufactured by Nissan Girdler Catalyst Co., Ltd.), and 30 ml of 1,4-butanediol were charged. After the inside of the reaction system was sufficiently substituted with nitrogen gas, 10 kg/cm$^2$ of hydrogen gas was introduced at normal temperature under pressure. Then, the temperature was elevated while stirring, and after the temperature reached 240° C., the reaction was carried out at the same temperature for additional 2 hours. After cooling, the reaction mixture was taken out and quantitative analysis of the reaction product was performed under the above analytical conditions. As a result, the conversion rate of the starting material melamine was 48.9% and it was confirmed that there were produced 2, 4-diamino-6-(4- hydroxybutylamino) -1,3, 5-triazine in a yield of 32.9%, 2-amino-4,6-bis(4-hydroxybutylamino)-1,3,5-triazine in a yield of 8.6%, and 2,4,6-tris(4-hydroxybutylamino)-1,3,5-triazine in a yield of 0.4%, respectively.

EXAMPLE 13

Reaction of melamine and 1,4-butanediol

In a stainless steel autoclave of an inner volume of 100 ml, 3.78 g (30 mmol) of melamine, 250 mg of 5% Pd—C catalyst (50% hydrated preparation), 250mg of Ni/NiO—$SiO_2/Al_2O_3$ catalyst (G-96D, manufactured by Nissan Girdler Catalyst Co., Ltd.), and 30 ml of 1,4-butanediol were charged. After the inside of the reaction system was sufficiently substituted with nitrogen gas, 10 kg/cm$^2$ of hydrogen gas was introduced under pressure at normal temperature. Then, the temperature was elevated while stirring, and after the temperature reached 220° C., the reaction was carried out at the same temperature for further 6 hours. After cooling, the reaction mixture was taken out and quantitative analysis of the reaction product was performed under the above analytical conditions. As a result, the conversion rate of the starting material melamine was 38.9% and it was confirmed that there were produced 2,4-diamino-6-(4-hydroxybutylamino) -1,3,5-triazine in a yield of 24.8%, 2-amino-4,6-bis(4-hydroxybutylamino)-1,3,5-triazine in a yield of 4.8%, and 2,4,6-tris(4-hydroxybutylamino)-1,3,5-triazine in a yield of 0.4%, respectively.

EXAMPLE 14

Reaction of melamine and 1,4-butanediol

In a stainless steel autoclave of an inner volume of 100 ml, 3.78 g (30 mmol) of melamine, 250 mg of 5% Pd—C catalyst (50% hydrated preparation), 250 mg of Ni/NiO—$ZrO_2/SiO_2$ catalyst (G-69B-RS, manufactured by Nissan Girdler Catalyst Co., Ltd.), and 30 ml of 1,4-butanediol were charged. After the inside of the reaction system was sufficiently substituted with nitrogen gas, 10 kg/cm$^2$ of hydrogen gas was introduced under pressure at normal temperature. Then, the temperature was elevated while stirring, and after the temperature reached 240° C., the reaction was carried out at the same temperature for further 2hours. After cooling, the reaction mixture was taken out and quantitative analysis of the reaction product was performed under the above analytical conditions. As a result, the conversion rate of starting material melamine was 84.8% and it was confirmed that there were produced 2,4-diamino-6-(4-hydroxybutylamino)-1,3,5-triazine in a yield of 30.7% , 2-amino-4,6-bis(4-hydroxybutylamino)-1,3,5-triazine in a yield of 29.3%, and 2,4,6-tris(4-hydroxybutylamino)-1,3,5-triazine in a yield of 6.5%, respectively.

EXAMPLE 15

Reaction of melamine and 1,5-pentanediol

In a stainless steel autoclave of an inner volume of 100 ml, 1.26 g (10 mmol) of melamine, 250 mg of 5% Pd—C catalyst (50% hydrated preparation), 250 mg of Ni/NiO—$SiO_2/Al_2O_3$ catalyst (G-96D, manufactured by Nissan Girdler Catalyst Co., Ltd.), and 30 ml of 1,5-pentanediol were charged. After the inside of the system was sufficiently substituted with nitrogen gas, 10 kg/cm$^2$ of hydrogen gas was introduced under pressure at normal temperature. Then, the temperature was elevated while stirring, and after the temperature reached 240° C., the reaction was carried out at the same temperature for further 2 hours. After cooling, the reaction mixture was taken out and quantitative analysis of the reaction product was performed under the above analytical conditions. As a result, the conversion rate of the starting material melamine was 90.6% and it was confirmed that there were produced 2,4-diamino-6-(5-hydroxypentylamino)-1,3,5-triazine in a yield of 29.5%, 2-amino-4,6-bis (5-hydroxypentylamino) -1,3,5-triazine in a yield of 37.0%, and 2,4,6-tris(5-hydroxypentylamino)-1,3, 5-triazine in a yield of 12.7%, respectively.

EXAMPLE 16

Reaction of melamine and 1,6-hexanediol

In a stainless steel autoclave of an inner volume of 100 ml, 1.26 g (10 mmol) of melamine, 250 mg of 5% Pd—C catalyst (50% hydrated preparation), 250 mg of Ni/NiO—$SiO_2/Al_2O_3$ catalyst (G-96D, manufactured by Nissan Girdler Catalyst Co., Ltd.), and 30 ml of 1,6-hexanediol were charged. After the inside of the reaction system was sufficiently substituted with nitrogen gas, 10 kg/cm$^2$ of hydrogen gas was introduced under pressure at normal temperature. Then, the temperature was elevated while stirring, and after the temperature reached 240° C., the reaction was carried out at the same temperature for further 2 hours. After cooling, the reaction mixture was taken out and quantitative analysis of the reaction product was performed under the above analytical conditions. As a result, the conversion rate of starting material melamine was 66.3% and it was confirmed that there were produced 2,4-diamino-6-(6-hydroxyhexylamino)-1,3,5-triazine in a yield of 43.9%, 2-amino-4,6-bis(6-hydroxyhexylamino)-1,3,5-triazine in a yield of 16.5%, and 2,4,6-tris(6-hydroxyhexylamino)-1,3,5-triazine in a yield of 4.0%, respectively.

EXAMPLE 17

Reaction of melamine and diethylene glycol

In a stainless steel autoclave of an inner volume of 100 ml, 1.26 g (10 mmol) of melamine, 250 mg of 5% Pd—C catalyst (50% hydrated preparation), 250mg of Ni/NiO—$SiO_2/Al_2O_3$ catalyst (G-96D, manufactured by Nissan Girdler Catalyst Co., Ltd.), and 30 ml of diethylene glycol were charged. After the inside of the reaction system was sufficiently substituted with nitrogen, 10 kg/cm$^2$ of hydrogen gas was introduced under pressure at normal temperature. Then, the temperature was elevated while stirring, and after the temperature reached 260° C., the reaction was carried out at the same temperature for further 2 hours. After cooling, the reaction mixture was taken out and quantitative analysis of the reaction product was performed under the above analytical conditions. As a result, the conversion rate of starting material melamine was 68.8% and it was confirmed that there were produced 2,4-diamino-6-(5-hydroxy-3-oxapentylamino)-1,3,5-triazine in a yield of 38.8%, 2-amino-4,6-bis(5-hydroxy-3-oxapentylamino)-1,3,5-triazine in a yield of 17.1%, and 2,4,6-tris(5-hydroxy-3-oxapentylamino)-1,3,5-triazine in a yield of 2.7%, respectively.

Hereinafter, examples of the second invention will be described.

EXAMPLE 18

Reaction of melamine and 1-butanol

In a stainless steel autoclave of an inner volume of 70 ml, 1.26 g (0.01 mol) of melamine, 25 mg of 5% Pd—C catalyst (50% hydrated preparation), 100 mg of iron powder, and 30 ml of butanol were charged. After the inside of the reaction system was sufficiently substituted with nitrogen gas, 40 kg/cm² of hydrogen gas was introduced. The temperature was elevated while stirring, and the reaction was carried out at a reaction temperature of 260° C. for 2 hours. Then, the reaction mixture was cooled and the contents were subjected to quantitative analysis. As a result, the conversion rate of starting material melamine was 82.6% and the obtained product contained 2,4-diamino-6-butylamino-1,3,5-triazine in a yield of 21.1%, 2-amino-4,6-bis(butylamino)-1,3,5-triazine in a yield of 38.5%, 2,4,6-tris(butylamino)-1,3,5-triazine in a yield of 16.1%, and 2,4-bis(butylamino)-6-dibutylamino-1,3,5-triazine in a yield of 3.5%, respectively.

EXAMPLE 19

Reaction of melamine and cyclohexanol

In a stainless steel autoclave of an inner volume of 70 ml, 1.26 g (0.01 mol) of melamine, 100 mg of 5% Pd—C catalyst (50% hydrated preparation), 100 mg of reduced iron powder, and 30 ml of cyclohexanol were charged. The inside of the reactor was sufficiently substituted with nitrogen, and then with 10 kg/cm² of hydrogen gas 5 times. Leaving 10 kg/cm² of hydrogen inside the reactor, the temperature was elevated while stirring and the reaction was carried out at a reaction temperature of 260° C. for 2 hours. Then the reaction mixture was cooled and the contents were subjected to quantitative analysis. As a result, the conversion rate of the starting material melamine was 64.6% and the obtained product contained 2,4-diamino-6-cyclohexylamino-1,3,5-triazine in a yield of 31.4%, 2-amino-4,6-bis(cyclohexylamino)-1,3,5-triazine in a yield of 25.8%, and 2,4,6-tris(cyclohexylamino)-1,3,5-triazine in a yield of 4.1%, respectively.

EXAMPLE 20

Reaction of melamine and 1,5-pentanediol

In a stainless steel autoclave of an inner volume of 100 ml, 1.26 g (10 mmol) of melamine, 250 mg of 5% Pd—C catalyst (50% hydrated preparation), 250 mg of reduced iron powder, and 30 ml of 1,5-pentanediol were charged. After the inside of the reaction system was sufficiently substituted with nitrogen gas, 10 kg/cm² of hydrogen gas was introduced under pressure at normal temperature. Then, the temperature was elevated to 260° C. while stirring, and after the temperature reached 260° C., the reaction was carried out at the same temperature for further 2hours. After cooling, the reaction mixture was taken out and quantitative analysis of the reaction product was performed under the above analytical conditions. As a result, the conversion rate of the starting material melamine was 83.8% and it was confirmed that there were produced 2,4-diamino-6-(5-hydroxypentylamino)-1,3,5-triazine in a yield of 34.2%, 2-amino-4,6-bis(5-hydroxypentylamino)-1,3,5-triazine in a yield of 32.1%, and 2,4,6-tris(5-hydroxypentylamino)-1,3,5-triazine in a yield of 7.1%, respectively.

EXAMPLE 21

Reaction of melamine and 1,5-pentanediol

In a stainless steel autoclave of an inner volume of 100 ml, 1.26 g (10 mmol) of melamine, 250 mg of 5% Pd—C catalyst (50% hydrated preparation), 250 mg of cobalt powder, and 30 ml of 1,5-pentanediol were charged. After the inside of the reaction system was sufficiently substituted with nitrogen gas, 10 kg/cm² of hydrogen gas was introduced under pressure at normal temperature. Then, the temperature was elevated to 260° C. while stirring, and after the temperature reached 260° C., the reaction was carried out at the same temperature for further 2 hours. After cooling, the reaction mixture was taken out and quantitative analysis of the reaction product was performed under the above analytical conditions. As a result, the reaction conversion rate of the starting material melamine was 90.0% and it was confirmed that there were produced 2,4-diamino-6-(5-hydroxypentylamino)-1,3,5-triazine in a yield of 33.1%, 2-amino-4,6-bis(5-hydroxypentylamino)-1,3,5-triazine in a yield of 37.6%, and 2,4,6-tris(5-hydroxypentylamino)-1,3,5-triazine in a yield of 7.2%, respectively.

EXAMPLE 22

Reaction of melamine and 1,4-butanediol

In a stainless steel autoclave of an inner volume of 100 ml, 1.26 g (10 mmol) of melamine, 250 mg of 5% Pd—C catalyst (50% hydrated preparation), 250 mg of reduced iron powder, and 30 ml of 1,4-butanediol were charged. After the inside of the reaction system was sufficiently substituted with nitrogen gas, 10 kg/cm² of hydrogen gas was introduced under pressure at normal temperature. Then, the temperature was elevated while stirring, and after the temperature reached 260° C., the reaction was carried out at the same temperature for additional 2hours. After cooling, the reaction mixture was taken out and quantitative analysis of the reaction product was performed under the above analytical conditions. As a result, the reaction conversion rate of the starting material melamine was 84.2% and it was confirmed that there were produced 2,4-diamino-6-(4-hydroxybutylamino)-1,3,5-triazine in a yield of 38.9%, 2-amino-4,6-bis(4-hydroxybutylamino)-1,3,5-triazine in a yield of 30.5%, and 2,4,6-tris(4-hydroxybutylamino)-1,3,5-triazine in a yield of 9.4%, respectively.

EXAMPLE 23

Reaction of melamine and 1,3-propanediol

In a stainless steel autoclave of an inner volume of 100 ml, 1.26 g (10 mmol) of melamine, 250 mg of 5% Pd—C catalyst (50% hydrated preparation), 250 mg of reduced iron powder, and 30 ml of 1,3-propanediol were charged. After the inside of the reaction system was sufficiently substituted with nitrogen gas, 10 kg/cm² of hydrogen gas was introduced under pressure at normal temperature. Then, the temperature was elevated while stirring, and after the temperature reached 260° C., the reaction was carried out at the same temperature for further 2 hours. After cooling, the reaction mixture was taken out and quantitative analysis of the reaction product was performed under the above analytical conditions. As a result, the conversion rate of starting material melamine was 84.5% and it was confirmed that there were produced 2,4-diamino-6-(3-hydroxypropylamino)-1,3,5-triazine in a yield of 33.4%, 2-amino-4,6-bis(3-hydroxypropylamino)-1,3,5-triazine in a yield of 35.2%, and 2,4,6-tris(3-hydroxypropylamino)-1,3,5-triazine in a yield of 14.6%, respectively.

EXAMPLE 24

Reaction of melamine and diethylene glycol

In a stainless steel autoclave of an inner volume of 100 ml, 1.26 g (10 mmol) of melamine, 250 mg of 5% Pd—C catalyst, 250 mg of reduced iron powder, and 30 ml of diethylene glycol were charged. After the inside of the reaction system was sufficiently substituted with nitrogen gas, 10 kg/cm² of hydrogen gas was introduced under pressure at normal temperature. Then, the temperature was elevated while stirring, and after the temperature reached 260° C., the reaction was carried out at the same temperature for further 2 hours. After cooling, the reaction mixture was taken out and quantitative analysis of the reaction product was performed under the above analytical conditions. As a result, the reaction conversion rate of the starting material melamine was 66.0% and it was confirmed that there were produced 2,4-diamino-6-(5-hydroxy-3-oxapentylamino)-1,3,5-triazine in a yield of 37.4%, 2-amino-4,6-bis(5-hydroxy-3-oxapentylamino)-1,3,5-triazine in a yield of 14.5%, and 2,4,6-tris(5-hydroxy-3-oxapentylamino)-1,3,5-triazine in a yield of 3.5%, respectively.

EXAMPLE 25

Reaction of melamine and diethylene glycol

In a stainless steel autoclave of an inner volume of 100 ml, 1.26 g (10 mmol) of melamine, 250 mg of 5% Pd—C catalyst, 250 mg of cobalt powder, and 30 ml of diethylene glycol were charged. After the inside of the reaction system was sufficiently substituted with nitrogen gas, 10 kg/cm$^2$ of hydrogen gas was introduced at normal temperature under pressure. Then, the temperature was elevated while stirring, and after the temperature reached 260° C., the reaction was carried out at the same temperature for further 2 hours. After cooling, the reaction mixture was taken out and quantitative analysis of the reaction product was performed under the above analytical conditions. As a result, the conversion rate of the starting material melamine was 74.4% and it was confirmed that there were produced 2,4-diamino-6-(5-hydroxy-3-oxapentylamino)-1,3,5-triazine in a yield of 35.4%, 2-amino-4,6-bis(5-hydroxy-3-oxapentylamino)-1,3,5-triazine in a yield of 19.6%, and 2,4,6-tris(5-hydroxy-3-oxapentylamino)-1,3,5-triazine in a yield of 3.9%, respectively.

EXAMPLE 26

Reaction of melamine and diethylene glycol

In a stainless steel autoclave of an inner volume of 100 ml, 1.26 g (10 mmol) of melamine, 250 mg of 5% Pd—C catalyst, 250 mg of manganese powder, and 30 ml of diethylene glycol were charged. After the inside of the reaction system was sufficiently substituted with nitrogen gas, 10 kg/cm$^2$ of hydrogen gas was introduced under pressure at normal temperature. Then, the temperature was elevated while stirring, and after the temperature reached 260° C., the reaction was carried out at the same temperature for further 2 hours. After cooling, the reaction mixture was taken out and quantitative analysis of the reaction product was performed under the above analytical conditions. As a result, the reaction conversion rate of the starting material melamine was 64.3% and it was confirmed that there were produced 2,4-diamino-6-(5-hydroxy-3-oxapentylamino)-1,3,5-triazine in a yield of 25.8%, 2-amino-4,6-bis(5-hydroxy-3-oxapentylamino)-1,3,5-triazine in a yield of 20.0%, and 2,4,6-tris(5-hydroxy-3-oxapentylamino)-1,3,5-triazine in a yield of 6.5%, respectively.

Comparative Example 1

Reaction of melamine and 1-butanol (Comparison with Examples 1 and 18)

In a stainless steel autoclave of an inner volume of 70 ml, 1.26 g (0.01 mol) of melamine, 25 mg of 5% Pd—C catalyst (50% hydrated preparation), and 30 ml of butanol were charged. After the inside of the reaction system was sufficiently substituted with nitrogen, 40 kg/cm$^2$ of hydrogen gas was introduced. The temperature was elevated while stirring and the reaction was carried out at a reaction temperature of 240° C. for 2 hours. Then the reaction mixture was cooled and the contents were subjected to quantitative analysis. As a result, the reaction conversion rate of the starting material melamine was 13.3% and the obtained product contained 2,4-diamino-6-butylamino-1,3,5-triazine in a yield of 11.2% and 2-amino-4,6-bis(butylamino)-1,3,5-triazine in a yield of 1.5%, respectively.

Comparative Example 2

Reaction of melamine and 1-butanol (Comparison with Example 1)

In a stainless steel autoclave of an inner volume of 70 ml, 1.26 g (0.01 mol) of melamine, 25 mg of CuO—Cr$_2$O$_3$ catalyst (G-13, manufactured by Nissan Girdler Catalyst Co., Ltd.), and 30 ml of butanol were charged. After the inside of the reaction system was sufficiently substituted with nitrogen, 10 kg/cm$^2$ of hydrogen gas was introduced. The temperature was elevated while stirring and the reaction was carried out at a reaction temperature of 240° C. for 1 hour. Then the reaction mixture was cooled and the contents were subjected to quantitative analysis. As a result, the conversion rate of the starting material melamine was 3.4% and the product obtained contained 2,4-diamino-6-butylamino-1,3,5-triazine in a yield of 3.0% and 2-amino-4,6-bis(butylamino)-1,3,5-triazine in a trace amount, respectively.

Comparative Example 3

Reaction of melamine and cyclohexanol (Comparison with Example 2)

In a stainless steel autoclave of an inner volume of 70 ml, 1.26 g (0.01 mol) of melamine, 25 mg of 5% Pd—C catalyst (50% hydrated preparation), and 30 ml of cyclohexanol were charged. The inside of the reactor was sufficiently substituted with nitrogen, and then with 10 kg/cm$^2$ of hydrogen gas 5 times. Leaving 10 kg/cm$^2$ of hydrogen inside the reactor, the temperature was elevated while stirring and the reaction was carried out at a reaction temperature of 260° C. for 2 hours. Then the reaction mixture was cooled and the contents were subjected to quantitative analysis. As a result, the reaction conversion rate of the starting material melamine was 15.5% and the obtained product contained 2,4-diamino-6-cyclohexylamino-1,3,5-triazine in a yield of 13.7% and 2-amino-4,6-bis(cyclohexylamino)-1,3,5-triazine in a yield of 1.6%, respectively.

Comparative Example 4

Reaction of melamine and 1,5-pentanediol (Comparison with Examples 3 to 5, 15, 20 and 21)

In a stainless steel autoclave of an inner volume of 100 ml, 1.26 g (10 mmol) of melamine, 250 mg of 5% Pd—C catalyst (50% hydrated preparation), and 30 ml of 1,5-pentanediol were charged. After the inside of the reaction system was sufficiently substituted with nitrogen gas, 10 kg/cm$^2$ of hydrogen gas was introduced under pressure at normal temperature. Then, the temperature was elevated while stirring, and after the temperature reached 260° C., the reaction was carried out at the same temperature for further 2 hours. After cooling, the reaction mixture was taken out and quantitative analysis of the reaction product was performed under the above analytical conditions. As a result, the reaction conversion rate of the starting material melamine was 46.0% and it was confirmed that there were produced 2,4-diamino-6-(5-hydroxypentylamino)-1,3,5-triazine in a yield of 32.6%, 2-amino-4,6-bis(5-hydroxypentylamino)-1,3,5-triazine in a yield of 8.2%, and 2,4,6-tris(5-hydroxypentylamino)-1,3,5-triazine in a yield of 1.5%, respectively and an obvious decrease in activity as compared with the mixed catalyst systems was confirmed.

Comparative Example 5

Reaction of melamine and 1,5-pentanediol (Comparison with Examples 3 to 5)

In a stainless steel autoclave of an inner volume of 100 ml, 1.26 g (10 mmol) of melamine, 250 mg of $CuO-Cr_2O_3-NiO-BaO$ catalyst (T-4364, manufactured by Nissan Girdler Catalyst Co., Ltd.), and 30 ml of 1,5-pentanediol were charged. After the inside of the reaction system was sufficiently substituted with nitrogen gas, 10 kg/cm$^2$ of hydrogen gas was introduced at normal temperature under pressure. Then, the temperature was elevated while stirring, and when the temperature reached 260° C., the reaction was carried out at the same temperature for further 2 hours. After cooling, the reaction mixture was taken out and quantitative analysis of the reaction product was performed under the above analytical conditions. As a result, the reaction conversion rate of the starting material melamine was 39.0% and it was confirmed that only about 4% of 2,4-diamino-6-(5-hydroxypentylamino)-1,3,5-triazine was produced as the product and an obvious decrease in activity as compared with the mixed catalyst systems was confirmed in the case of the single catalyst.

Comparative Example 6

Reaction of melamine and 1,4-butanediol (Comparison with Examples 6, 11 and 22)

In a stainless steel autoclave of an inner volume of 100 ml, 1.26 g (10 mmol) of melamine, 250 mg of 5% Pd—C catalyst, and 30 ml of 1,4-butanediol were charged. After the inside of the reaction system was sufficiently substituted with nitrogen gas, 10 kg/cm$^2$ of hydrogen gas was introduced under pressure at normal temperature. Then, the temperature was elevated while stirring, and after the temperature reached 260° C., the reaction was carried out at the same temperature for further 2 hours. After cooling, the reaction mixture was taken out and quantitative analysis of the reaction product was performed under the above analytical conditions. As a result, the reaction conversion rate of the starting material melamine was 48.1% and it was confirmed that there were produced only 22.0% of 2,4-diamino-6-(4-hydroxybutylamino)-1,3,5-triazine and 6.7% of 2-amino-4,6-bis (4-hydroxybutylamino)-1,3,5-triazine as the products, and an obvious decrease in activity as compared with the mixed catalyst systems was confirmed.

Comparative Example 7

Reaction of melamine and diethylene glycol (Comparison with Examples 9, 17 and 24 to 26)

In a stainless steel autoclave of an inner volume of 100 ml, 1.26 g (10 mmol) of melamine, 250 mg of 5% Pd—C catalyst, and 30 ml of diethylene glycol were charged. After the inside of the reaction system was sufficiently substituted with nitrogen gas, 10 kg/cm$^2$ of hydrogen gas was introduced under pressure at normal temperature. Then, the temperature was elevated while stirring, and after the temperature reached 260° C., the reaction was carried out at the same temperature for further 2 hours. After cooling, the reaction mixture was taken out and quantitative analysis of the reaction product was performed under the above analytical conditions. As a result, the reaction conversion rate of the starting material melamine was 21.5% and it was confirmed that there was produced only 13.5% of 2,4-diamino-6-(5-hydroxy-3-oxapentylamino)-1,3,5-triazine as the product, and an obvious decrease in activity as compared with the mixed catalyst systems was confirmed.

Comparative Example 8

Reaction of melamine and diethylene glycol (Comparison with Examples 9 and 24)

In a stainless steel autoclave of an inner volume of 100 ml, 1.26 g (10 mmol) of melamine, 250 mg of $CuO-Cr_2O_3-NiO-BaO$ catalyst (T-4364, manufactured by Nissan Girdler Catalyst Co., Ltd.), and 30 ml of diethylene glycol were charged. After the inside of the reaction system was sufficiently substituted with nitrogen gas, 10 kg/cm$^2$ of hydrogen gas was introduced under pressure at normal temperature. Then, the temperature was elevated while stirring, and after the temperature reached 260° C., the reaction was carried out at the same temperature for further 2 hours. After cooling, the reaction mixture was taken out and quantitative analysis of the reaction product was performed under the above analytical conditions. As a result, the reaction conversion rate of the starting material melamine was 11% and it was confirmed that there were produced only about 2% of 2,4-diamino-6-(5-hydroxy-3-oxapentylamino)-1,3,5-triazine together with many byproducts and an obvious decrease in activity as compared with the mixed catalyst systems was confirmed.

Comparative Example 9

Reaction of melamine and 1,4-butanediol (Comparison with Examples 12, 13 and 14)

In a stainless steel autoclave of an inner volume of 100 ml, 3.78 g (30 mmol) of melamine, 250 mg of 5% Pd—C catalyst (50% hydrated preparation), and 30 ml of 1,4-butanediol were charged. After the inside of the reaction system was sufficiently substituted with nitrogen gas, 10 kg/cm$^2$ of hydrogen gas was introduced under pressure at normal temperature. Then, the temperature was elevated while stirring and after the temperature reached 240° C., the reaction was carried out at the same temperature for further 2 hours. After cooling, the reaction mixture was taken out and quantitative analysis of the reaction product was performed under the above analytical conditions. As a result, the reaction conversion rate of the starting material melamine was 26.4% and it was confirmed that there were produced 2,4-diamino-6-(4-hydroxybutylamino)-1,3,5-triazine in a yield of 6.2% and 2-amino-4,6-bis(4-hydroxybutylamino)-1,3,5-triazine in a yield of 0.4%, respectively, and an obvious decrease in activity as compared with the reactions using mixed catalyst systems was confirmed.

EFFECT OF THE INVENTION

According to the method of the present invention, N-substituted melamine derivatives, in particular, N-substituted melamine derivatives having a hydroxyl group, which are useful compounds widely used for various paints, adhesives, resin materials, flame retardant materials can be produced from melamine or N-substituted melamine derivatives of the general formula (I) and alcohols of the general formula (II) under relatively mild reaction conditions by simple reaction operations and moreover by-producing only water.

In the present invention, by reacting in the presence of hydrogen using a catalyst system comprising a hydrogenation catalyst and a dehydrogenation catalyst, or a catalyst system comprising a hydrogenation catalyst and a selected metal, a reaction can be achieved that has extraordinarily excellent activity as compared with the conventional method that performs reaction using a metal catalyst in the presence of hydrogen. As a result, reaction conversion rate of a starting material melamine increases and it becomes possible to produce highly substituted melamine derivatives.

The various modified N-substituted melamine derivatives, which are products obtained by the present invention, can be obtained generally as mixtures. The products can be separated by general separation methods for organic substances in highly pure or pure forms to provide for the above various applications.

Depending on the application (in particular, in the case of modifying additives for resins, etc.), the reaction mixture can be used as it is without separation.

Further, the N-substituted melamine derivatives that are easily obtained by the present reaction include those compounds whose synthesis has heretofore been relatively difficult or which have been expensive. As for their physical properties, there are many compounds that are interesting in solubilities in water and various organic solvents, stability at high temperatures, melting points, boiling points, basisity and their applications will broaden more than in the past.

What is claimed is:

1. A synthetic method of melamine compounds by introducing a substituent to an amino group on a triazine ring carbon atom of melamine, characterized by heating melamine and an alcohol in the presence of a mixed catalyst comprising a hydrogenation catalyst and a dehydrogenation catalyst, and hydrogen to allow reaction, wherein the mixed catalyst is a solid catalyst for a non-uniform system, and the dehydrogenation catalyst is a metal oxide-mixed system or a mixed metal oxide, selected from the group consisting of $CuO-Cr_2O_3$, $CuO-Cr_2O_3-BaO$, $CuO-Cr_2O_3-NiO-BaO$, $ZnO-Cr_2O_3$, $ZnCr_2O_4$, $ZnFe_2O_4$, $Ni/NiO-SiO_2/Al_2O_3$, and $Ni/NiO-ZrO_2/SiO_2$.

2. A synthetic method of melamine compounds according to claim 1, wherein the alcohols used in the reaction are alcohols of the formula (II)

$$R-OH \qquad (II)$$

wherein R is $C_{1-20}$ alkyl group (the alkyl may optionally be substituted by one or more substituents, which are different or the same, selected from the group consisting of hydroxyl, $C_{1-6}$ alkoxy, $C_{1-6}$ hydroxyalkoxy, $C_{2-10}$ hydroxyalkoxyalkoxy, $C_{2-6}$ alkoxycarbonyl and a phenyl).

3. A synthetic method of melamine compounds according to claim 1, wherein the melamine compounds obtained by the synthetic method according to claim 1 are melamine compounds of the formula (III)

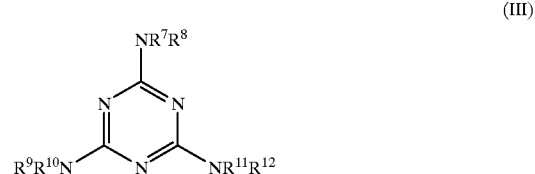

wherein at least one of groups $R^7, R^8, R^9, R^{10}, R^{11}$ and $R^{12}$ is a substituent R (R is $C_{1-20}$ alkyl (the alkyl may optionally be substituted by one or more substituents, which are different or the same, selected from the group consisting of hydroxyl, $C_{1-6}$ alkoxy, $C_{1-6}$ hydroxyalkoxy, $C_{2-10}$ hydroxyalkoxyalkoxy, $C_{2-6}$ alkoxycarbonyl and phenyl)), and other groups are hydrogen.

4. A synthetic method of melamine compounds according to claim 1, wherein the hydrogenation catalysts used in the reaction are catalysts that contain one or more metals selected from iron, cobalt, nickel, copper, ruthenium, rhodium, palladium, iridium and platinum.

5. A synthetic method of melamine compounds according to claim 1, wherein the hydrogenation catalysts used in the reaction are catalysts that contain one or more metals selected from cobalt, nickel, ruthenium, rhodium, palladium and platinum.

6. A synthetic method of melamine compounds according to claim 1, wherein the hydrogenation catalysts used in the reaction are catalysts that contain one or more metals selected from nickel, ruthenium, rhodium and palladium.

7. A synthetic method of melamine compounds by introducing a substituent to an amino group on a triazine ring carbon atom of melamine, characterized by heating melamine and an alcohol in the presence of a hydrogenation catalyst and hydrogen with addition/coexistence of a metal to allow reaction, wherein the hydrogenation catalysts are carried catalysts, the hydrogenation catalysts are catalysts that contain one or more metals selected from nickel, copper, ruthenium, rhodium, palladium, iridium and platinum, the metals are powder, and the metals to be added and allowed to coexist in the reaction are metal powder selected from iron, cobalt and manganese.

8. A synthetic method of melamine compounds according to claim 7, wherein the alcohols used in the reaction are alcohols of the formula (II)

$$R-OH \qquad (II)$$

wherein R is $C_{1-20}$ alkyl group (the alkyl may optionally be substituted by one or more substituents, which are different or the same, selected from the group consisting of hydroxyl, $C_{1-6}$ alkoxy, $C_{1-6}$ hydroxyalkoxy, $C_{2-10}$ hydroxyalkoxyalkoxy, $C_{2-6}$ alkoxycarbonyl and a phenyl).

9. A synthetic method of melamine compounds according to claim 7, wherein the melamine compounds obtained by the synthetic method according to claim 7 are melamine compounds of the formula (III)

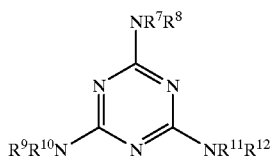

(III)

wherein at least one of groups $R^7$, $R^8$, $R^9$, $R^{10}$, $R^{11}$ and $R^{12}$ is a substituent R (R is $C_{1-20}$ alkyl (the alkyl may optionally be substituted by one or more substituents, which are different or the same, selected from the group consisting of hydroxyl, $C_{1-6}$ alkoxy, $C_{1-6}$ hydroxyalkoxy, $C_{2-10}$ hydroxyalkoxyalkoxy, $C_{2-6}$ alkoxycarbonyl and phenyl)), and other groups are hydrogen.

10. A synthetic method of melamine compounds according to claim 7, wherein the hydrogenation catalysts used in the reaction are catalysts that contain one or more metals selected from nickel, ruthenium, palladium and platinum.

11. A synthetic method of melamine compounds according to claim 7, wherein the hydrogenation catalysts used in the reaction are catalysts that contain palladium.

12. A synthetic method of melamine compounds according to claim 7, wherein the hydrogenation catalysts are palladium carried on activated carbon.

13. A synthetic method of melamine compounds according to claim 7, wherein the metals to be added and allowed to coexist in the reaction are metal powder selected from iron and cobalt.

\* \* \* \* \*